(12) United States Patent
Wippenbeck et al.

(10) Patent No.: US 10,768,087 B2
(45) Date of Patent: Sep. 8, 2020

(54) COUNTING COMPARTMENT AND METHOD FOR SAMPLE ANALYSIS

(71) Applicant: MINITÜB GMBH, Tiefenbach (DE)

(72) Inventors: Georg Wippenbeck, Aham (DE); Christian Simmet, Landshut (DE)

(73) Assignee: MINITUB GMBH, Tiefenbach (DE)

( * ) Notice: Subject to any disclaimer, the term of this patent is extended or adjusted under 35 U.S.C. 154(b) by 0 days.

(21) Appl. No.: 16/071,674

(22) PCT Filed: Jan. 30, 2017

(86) PCT No.: PCT/EP2017/051933
§ 371 (c)(1),
(2) Date: Jul. 20, 2018

(87) PCT Pub. No.: WO2017/129819
PCT Pub. Date: Aug. 3, 2017

(65) Prior Publication Data
US 2019/0025179 A1 Jan. 24, 2019

(30) Foreign Application Priority Data

Jan. 28, 2016 (EP) ..................................... 16153189

(51) Int. Cl.
*G01N 15/06* (2006.01)
*G01N 21/03* (2006.01)
(Continued)

(52) U.S. Cl.
CPC .............. *G01N 15/06* (2013.01); *B01L 3/508* (2013.01); *G01N 15/1425* (2013.01); *G01N 15/1434* (2013.01); *G01N 21/0303* (2013.01); *G01N 33/487* (2013.01); *G02B 21/14* (2013.01); *B01L 3/502715* (2013.01); *B01L 2200/025* (2013.01);
(Continued)

(58) Field of Classification Search
CPC ............... B01L 3/502715; B01L 3/508; B01L 2200/025; B01L 2200/0647; B01L 2300/0041; B01L 2300/0816; B01L 2300/0851; B01L 2300/0854; B01L 2300/0877; G01N 15/06; G01N 15/1425; G01N 15/1434; G01N 21/0303; G01N 33/487; G01N 2015/0693; G01N 2015/144; G01N 2015/1486; G01N 2021/0321; G01N 2021/0382; G01N 2021/0389;
(Continued)

(56) References Cited

U.S. PATENT DOCUMENTS 5,214,593 A 5/1993 Magnussen, Jr. et al.
5,371,020 A 12/1994 Frischauf
(Continued)

FOREIGN PATENT DOCUMENTS

WO 99/58954 A1 11/1999
WO 2014038399 A1 3/2014

*Primary Examiner* — Mark R Gaworecki
(74) *Attorney, Agent, or Firm* — Saliwanchik, Lloyd & Eisenschenk (57) ABSTRACT

The invention relates to a counting chamber for a microscope, adjustable in height. The method measures a cell count at two different chamber heights and deduces the concentration of particles without an exact calibration of the absolute height, as the height difference gives a measurement of the "missing" volume and therefore an estimate of the particle concentration.

19 Claims, 8 Drawing Sheets measurement window (51) Int. Cl.
    *G01N 15/14*     (2006.01)
    *B01L 3/00*      (2006.01)
    *G01N 33/487*    (2006.01)
    *G02B 21/14*     (2006.01)
    *G02B 21/26*     (2006.01)

(52) U.S. Cl.
    CPC . *B01L 2200/0647* (2013.01); *B01L 2300/041* (2013.01); *B01L 2300/0816* (2013.01); *B01L 2300/0851* (2013.01); *B01L 2300/0854* (2013.01); *B01L 2300/0877* (2013.01); *G01N 2015/0693* (2013.01); *G01N 2015/144* (2013.01); *G01N 2015/1486* (2013.01); *G01N 2021/0321* (2013.01); *G01N 2021/0382* (2013.01); *G01N 2021/0389* (2013.01); *G01N 2201/066* (2013.01); *G01N 2201/0662* (2013.01); *G02B 21/26* (2013.01)

(58) Field of Classification Search
    CPC ..... G01N 2201/066; G01N 2201/0662; G02B 21/14; G02B 21/26
    See application file for complete search history.

(56) References Cited

U.S. PATENT DOCUMENTS

| | | |
|---|---|---|
| 2015/0118708 A1 | 4/2015 | Hammond et al. |
| 2016/0145555 A1* | 5/2016 | Ingber .................... C12M 23/16 435/29 |

* cited by examiner

Figure 1 A and B

Figure 1 C and D

Figure 5 ial Application Number PCT/EP2017/051933, filed
COUNTING COMPARTMENT AND METHOD FOR SAMPLE ANALYSIS

CROSS REFERENCE TO RELATED APPLICATIONS

This application is a National Stage Application of International Application Number PCT/EP2017/051933, filed Jan. 30, 2017; which claims priority to European Patent Application No. 16153189.2, filed Jan. 28, 2016.

The present invention relates to a counting compartment or counting chamber for analyzing samples comprising cells or particles, said counting compartment or chamber comprising at least two different depths provided by the bottom and top measurement window. The present invention further relates to a counting device comprising the counting compartment or counting chamber of the present invention. The present invention further relates to a method for analyzing samples comprising cells or particles, comprising the step of determining the difference between the value measured at the at least two different depths of a counting compartment or counting chamber. The present invention further relates to a method for analyzing samples comprising cells or particles, comprising the step of controlling the depth of a counting compartment.

BACKGROUND OF THE INVENTION

When examining body fluids, it is often desirable to study samples of such biological material under the microscope over a certain time. When examining sperm, for example, the aim is to establish how many spermatozoa are present in the sample and also how motile they are and how their morphology is. When examining blood samples, for example, the aim is to establish how many red and/or white blood cells are present in the sample and also how their morphology is.

To carry out this investigation, a sample of a certain thickness is to be subjected to microscopic examination in a counting compartment, using a grid built into the eyelens of the microscope. Such a grid may be divided into a hundred squares, and the number of cells (such as spermatozoa or blood cells) in each of a representative number of squares can be counted by the investigator in order to determine the total number of cells in the whole grid area. Such a grid may also be provided in the counting compartment.

From U.S. Pat. Nos. 4,911,782 and 5,200,152 a method is known for conducting such determinations with the aid of a counting compartment formed by two transparent plates joined together by a connecting layer composed of a cured plastic.

From U.S. Pat. No. 6,551,554 B1 and EP patent No. 0 809 815 B1 a counting device is known, which comprises two transparent plates which are held at a fixed distance from each other and joined together by a connecting layer, and at least one counting compartment which is situated between the plates, bounded by the connecting layer and fitted with an inlet and an outlet. The connecting layer contains material particles which are separate from one another and have a size that determines the depth of the counting compartment, which material particles are substantially in contact with the two plates.

For a correct quantitative evaluation of a sample it is required that the correct depth between the two glass plates of the counting device is maintained throughout the complete counting area. It is also required that there is no variation between counting devices in order to allow a correct quantitative evaluation of all samples to be analyzed using such a device. However, this counting device is a one-way device and requires a new counting area for each sample thus raising high requirements for uniformity of the devices. The way of loading the device as well as the quality of the sample can influence the result of such an evaluation. As the two glass plates are firmly attached to each other, the sample must pass through a very small gap into the counting area (typically between 10 and 100 µm), being thus exposed to any kind of blocking or sieving effects developing at such a small gap. The qualitative analysis of a sample of cells like sperm requires a completely inert and non-toxic environment to allow observation of unimpaired motility and morphology of the sperm. Typically counting devices consisting of two glass plates use a glue or adhesive to attach the glass plates to each other. Such binding material often is toxic to sperm and impairs motility and or morphology of the sperm.

There is a need in the art for improved counting devices and methods for analysing samples comprising cells and/or particles, which in particular allow to obtain accurate and improved measurement results.

SUMMARY OF THE INVENTION

According to the present invention this object is solved by a counting compartment for analyzing samples comprising cells or particles, said counting compartment comprising
(1) a lid or top part comprising a top measurement window;
(2) a bottom part comprising a bottom measurement window; and
(3) at least two different depths provided by the bottom and top measurement window.

According to the present invention this object is solved by a counting device for analyzing samples comprising cells or particles comprising
 the counting compartment of the present invention,
 a control unit,
 filling means,
 removing means,
 a light microscope and/or a fluorescence microscope, and
 optionally, sensor(s).

According to the present invention this object is solved by a method for analyzing samples comprising cells or particles,
 preferably using the counting compartment of the present invention and/or the counting device of the present invention,
 comprising the step of
 determining the difference between the value measured at the at least two different depths of a counting compartment.

According to the present invention this object is solved by a method for analyzing samples comprising cells or particles,
 comprising the step of
 controlling the depth of a counting compartment,
   preferably by z axis-calibration or by sensor measurement.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "5 to 100" should be interpreted to include not only the explicitly recited values of 5 to 100, but also include individual values and sub-ranges within the indicated range. Thus, included in this numerical range are individual values such as 5, 6, 7, 8, 9, 10, 11, 12, 13 . . . 97, 98, 99, 100 and sub-ranges such as from 10 to 40, from 12 to 17 and 41 to 50, etc. This same principle applies to ranges reciting only one numerical value, such as "about 10". Furthermore, such an interpretation should apply regardless of the breadth of the range or the characteristics being described. Also it is to be understood that ranges may differ depending on the institute/facility where the measurements are being performed, methodology of measurement, type of tissue, and technique of tissue collection.

Counting Compartment or Chamber

The present invention provides a counting compartment or counting chamber for analyzing samples comprising cells or particles.

Said counting compartment or counting chamber comprises:
  (1) a lid or top part comprising a top measurement window;
  (2) a bottom part comprising a bottom measurement window;
  (3) at least two different depths provided by the bottom and top measurement window.

Figure 1:
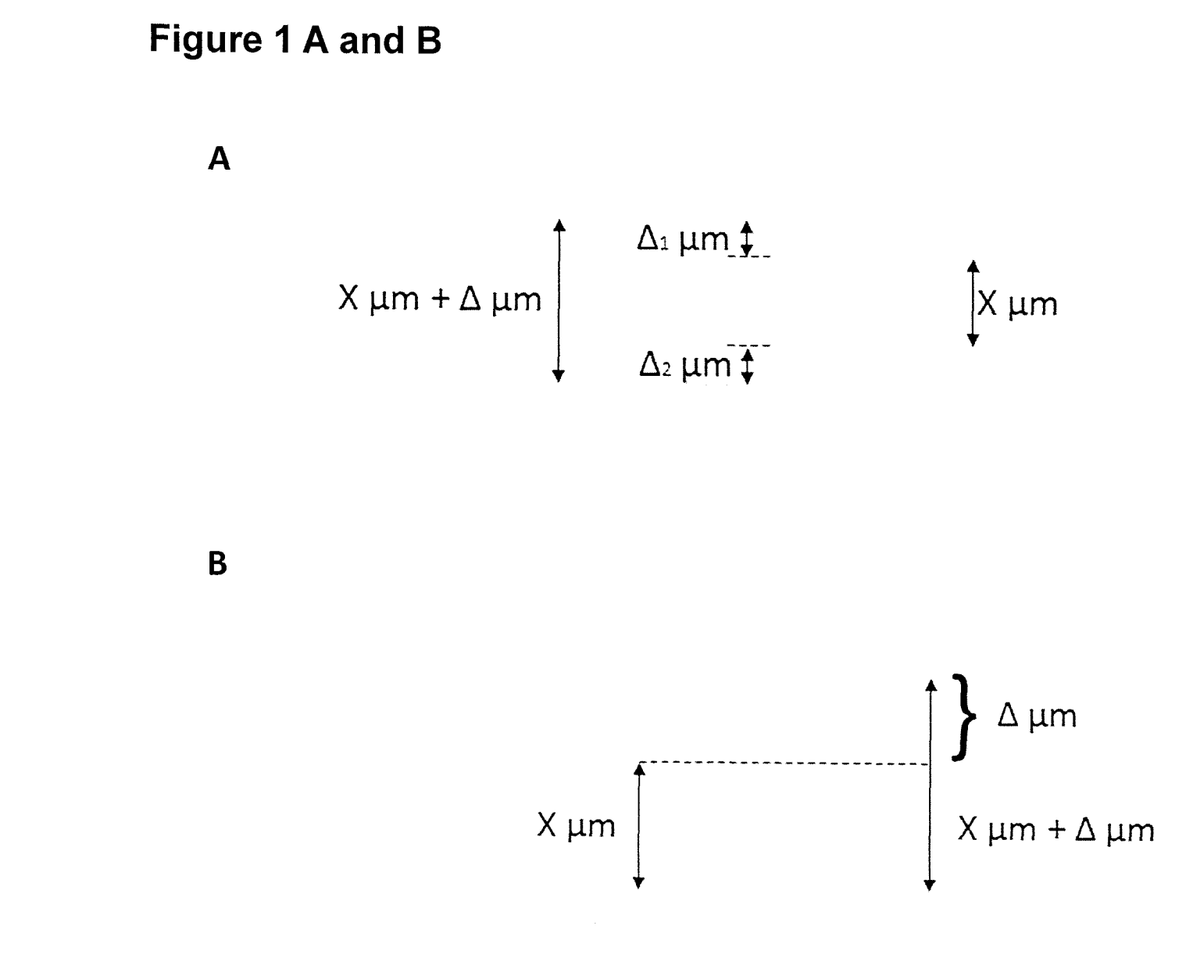
FIG. 1. Schematic presentation of the counting compartment with at least two different depths.

The at least two different depths of the counting compartment are provided by the bottom and top measurement window and can preferably be achieved by the following embodiments:

In one embodiment (embodiment (i)), the bottom and/or top measurement window comprise step(s).

One or both of the measurement windows comprise a step. The counting compartment can be configured such that when the lid/top part closes on the bottom part the step of each of both measurement windows is on top of each other (i.e. super-imposed), thereby forming two different depths; or they are not on top of each other, thereby forming more than two different depths.

See, for example FIG. 1A.

The measurement windows can also comprise more than one such step.

In one embodiment (embodiment (ii)), one of the bottom or top measurement window is placed with inclination.

See, for example FIG. 1B.

In one embodiment (embodiment (iii)), one of the bottom or top measurement window is placed parallel to the other measurement window and is provided with a inclined plane on the side facing the sample liquid.

See, for example FIG. 1C.

Furthermore, the at least two different depths of the counting compartment can also be provided by movement, namely by moving the lid or top part and/or the bottom part of the counting compartment, such as with a spindle with motor.

See, for example FIG. 1D.

Preferably, the bottom and/or top measurement window is made of a transparent material, such as glass or plastic.

In one embodiment, the at least two different depths provided by the bottom and top measurement window are in the range of about 5 to about 100 µm, preferably about 10 µm to 40 µm, for example 10 µm and 20 µm.

Preferably, the difference between the two different depths provided by the bottom and top measurement window is at least the size or height of a monolayer of the cells or particles of the sample to be analyzed.

The counting compartment of the present invention can further comprise
  (4) means for moving the lid or top part.

The counting compartment of the present invention can further comprise
  (5) an inlet and outlet.

Preferably, the means for moving the lid or top part comprise magnetic means and optionally spacer.

Examples for magnetic means are permanent electro magnet(s). The magnetic means can be comprised in the lid or top part and/or the bottom part.

Examples for spacer are spring-loaded spacers. The spacer(s) can be comprised in the lid or top part and/or the bottom part.

Furthermore, (micrometer) screws or gauges can be comprised in the lid or top part and/or the bottom part.

In one embodiment, the lid or top part and the bottom part of the counting department/chamber of the invention are manufactured by high precision manufacturing. In such embodiment, no (micrometer) screws or gauges are necessary.

In one embodiment, the lid or top part is moved by mechanic means, such as a spindle with an attached motor.

The lid or top part and the bottom part are preferably configured such that they form the bottom, lid and side walls of the counting compartment or counting chamber.

In one embodiment, the lid or top part and the bottom part are made of steel, such as stainless steel.

In one embodiment, the lid or top part and the bottom part are made of ceramics or plastic or using a coating of yet another material to provide certain properties to the device or a combination of materials and manufacturing technologies.

The inlet and/or outlet can be part of the lid or top part and/or the bottom part.

In a preferred embodiment, the counting compartment or counting chamber of the present invention is a flow-through counting compartment or counting chamber.

In such embodiment, the counting compartment or counting chamber of the present invention is provided/configured such that it can be connected with pumps, control units etc.

In one embodiment, the counting compartment further comprises
  a heating unit, and/or
  a positioning unit.

A heating unit is suitable for controlling the temperature of the sample to be analyzed, such as in case of a semen sample. A positioning unit is suitable for moving the counting compartment. The positioning and heating unit can be separate but also jointed into one system.

In one embodiment, the counting compartment of the present invention, further comprises
a grid in one of the measurement windows.
Said grid allows a manual count.
Preferably, the samples comprising cells or particles are
semen samples
blood samples,
such as serum, whole blood,
samples comprising particles,
such as plastic particles, ceramic particles, liposomes or cell derivatives,
samples of microorganisms,
such as those who are used in bioreactors or for sewage treatment,
algae samples.

In one embodiment, the counting compartment is configured to be used for determining the number of cells or particles. In a preferred embodiment, such cells are spermatozoa or blood cells, e. g. red blood cells. In a preferred embodiment, the cells are spermatozoa.

Counting Device Comprising the Counting Compartment or Chamber

The present invention provides a counting device for analyzing samples comprising cells or particles.
Said counting device comprises:
the counting compartment or counting chamber of the present invention,
a control unit,
filling means,
such as an injection pump, injection syringe, flexible-tube pump, dilutors, tubing,
removing means,
such as a draw-off pump,
a light microscope and/or a fluorescence microscope,
preferably a phase contrast microscope,
preferably comprising a motorized positioning unit, and/or a heating unit,
and
optionally, sensor(s),
such as a white-light interferometer sensor, current sensor, inductive sensor, capacitive sensor or optical sensor.
Said sensor(s) of the counting device are for determining and obtaining the depth(s) of the counting compartment.

In one embodiment, the counting device of the present invention, further comprises
processing, analyzing and/or evaluating system and software, such as AndroVision® CASA Software (of Minitüb GmbH, Germany).

In one embodiment, the counting device of the present invention, further comprises
further sensor(s), such as current sensor, inductive sensor, capacitive sensor, optical sensor(s).

In one embodiment, the counting device of the present invention, further comprises
a grid in the ocular of the light microscope or in one of the measurement windows of the counting compartment or chamber.
Said grid allows a manual count.
Preferably, the samples comprising cells or particles are
semen samples
blood samples,
such as serum, whole blood,
samples comprising particles,
such as plastic particles, ceramic particles, liposomes or cell derivatives,
samples of microorganisms,
such as those who are used in bioreactors or for sewage treatment,
algae samples.

The counting device of the present invention can be designed for the manual or automated use.
In one embodiment, the counting device of the present invention is (fully) automatized.

In one embodiment, the counting device is configured to be used for determining the number of cells or particles. In a preferred embodiment, such cells are spermatozoa or blood cells, e. g. red blood cells. In a preferred embodiment, the cells are spermatozoa.

Methods for Analysing Samples

The present invention provides a first method for analyzing samples comprising cells or particles.
Said first method comprises the step of
determining the difference between the value measured at the at least two different depths of a counting compartment.

Determining Said Difference can be Used in the Following Ways:

1. as mathematically determined value:
preferably for determining the number of cells or particles in a sample (as described herein in further detail).
Furthermore the mathematically determined value allows to neglect contamination (i.e. dirt and/or old cells or particles) for the measurement, because such contamination is usually present on all areas of all the depths and can therefore be subtracted during determination of the mathematical determined value.

2. as method for verifying/testing the absolute distances between the measurement windows at the first and second depth (i.e. at the smaller and higher depth):
In case that the difference value differs not more than x % from the measurement value at the higher and/or smaller depth, then one can assume that the desired/set depths were attained and the measurement value at the higher and/or smaller depth could directly be used as the sample value. The deviation "x" depends on the set-up, the application and/or the desired precision.

3. a combination of 1. and 2.

Said method of the present invention preferably uses the counting compartment or counting chamber of the present invention and/or the counting device of the present invention.

Preferably and as discussed above, the samples comprising cells or particles are
semen samples
blood samples,
such as serum, whole blood,
samples comprising particles,
such as plastic particles, ceramic particles, liposomes or cell derivatives,
samples of microorganisms,
such as those who are used in bioreactors or for sewage treatment,
algae samples.

In one embodiment, the method of the present invention comprises the steps of
(1) providing a sample comprising cells and/or particles to be analyzed,
which is preferably homogenized;

(2) providing the counting compartment or counting chamber of the present invention and/or the counting device of the present invention;

(3) loading the counting compartment with the sample, wherein the lid or top part is in open position;

(4) closing the counting compartment by closing the lid or top part;

(5) determining the value to be measured at the first depth of the at least two different depths and at the second depth of the at least two different depths;

(6) determining the difference between the two values measured in step (5) and obtaining the sample value, (7) opening the counting compartment by opening or lifting the lid or top part;

(8) rinsing the counting compartment and thereby removing the sample.

After one measurement cycle, i.e. after rinsing the counting compartment (step (8)), the next sample can be analyzed.

Preferably, the sample value to be measured is the number of cells or particles in the sample, such as the number of spermatozoa/concentration of spermatozoa.

In one embodiment of the first method for analysing samples comprising cells or particles, the number of cells or particles is measured by identifying and counting each cell in the sample individually and, optionally, by determining, for each cell individually, based on defined parameters, such as cell motility, cell morphology, cell viability etc., whether or not such cell is to be added towards the number of cells to be measured. The method according to the present invention is particularly suitable to count the number of spermatozoa in a sample, such spermatozoa being characterized by a set of defined characteristics, as determined by a user/operator of the counting device according to the present invention. The characteristics may be chosen depending on the intended use of the cells. In one embodiment, the method according to the present invention neither involves the lysis of cells nor the numerical determination of an absorbance value caused by an analyte/biomolecule dissolved in the (liquid) sample. In one embodiment, the method according to the present invention does not involve the numerical determination of a light scattering value caused by an analyte or cell or particle in the (liquid) sample. In embodiments, where the number of cells or particles is determined, such number of cells preferably is an integer value.

In one embodiment, the method of the present invention comprises further analysis of the sample, such as the analysis/evaluation of
cell motility;
cell morphology;
cell viability;
further characteristics, such as cell acrosome integrity, cell mitochondrion activity, cell deoxyribonucleic acid integrity. Such characteristics may be used to classify cells and determine whether or not a cell is to be counted towards the number of cells to be measured. For example a cell, e.g. a spermatozoon, which is immobile or not viable, may, in one embodiment, not be counted towards the number of cells to be measured. Depending on the chosen characteristics/parameters, different subsets of cells in a sample may be counted.

The present invention provides a further method for analyzing samples comprising cells or particles.

Said further method comprises the step of
controlling the depth of a counting compartment,
preferably by
z axis-calibration, or
sensor measurement,
such as a white-light interferometer sensor, current sensor, capacitive sensor or laser sensor.

Preferably and as discussed above, the samples comprising cells or particles are
semen samples
blood samples,
such as serum, whole blood,
samples comprising particles,
such as plastic particles, ceramic particles, liposomes or cell derivatives,
samples of microorganisms,
such as those who are used in bioreactors or for sewage treatment,
algae samples.

In one embodiment, the method of the present invention comprises the steps of (1) providing a sample comprising cells and/or particles to be analyzed,
which is preferably homogenized;

(2) providing a counting compartment comprising a marking in the lid and a marking in the bottom or in its measurement windows (which allows z axis-calibration), and/or providing a counting compartment or device comprising a sensor (such as a white-light interferometer sensor, current sensor, capacitive sensor or laser sensor), (3) loading the counting compartment with the sample, (4) measuring the distance between the marking in the lid and the marking in the bottom or in its measurement windows (i.e. z axis-calibration) or by measuring the depth with the sensor;
and then determining the depth of the loaded counting department;
optionally comprising the use of a correction value or factor;

(5) determining the sample value(s) to be measured, (6) opening the counting compartment by opening or lifting the lid or top part;

(7) rinsing the counting compartment and thereby removing the sample.

After one measurement cycle, i.e. after rinsing the counting compartment (step (7)), the next sample can be analyzed.

Preferably, the sample value to be measured is the number of cells or particles in the sample, such as the number of spermatozoa/concentration of spermatozoa.

Depending on the sensor(s) used: the order of steps (3) and (4) can change, thus, step (4) can follow step (3) or step (3) can follow step (4).

In one embodiment of the further method for analysing samples comprising cells or particles, the number of cells or particles is measured by identifying and counting each cell in the sample individually and, optionally, by determining, for each cell individually, based on defined parameters, such as cell motility, cell morphology, cell viability etc., whether or not such cell is to be added towards the number of cells to be measured. The method according to the present invention is particularly suitable to count the number of spermatozoa in a sample, such spermatozoa being characterized by a set of defined characteristics, as determined by a user/operator of the counting device according to the present invention. The characteristics may be chosen depending on the intended use of the cells. In one embodiment, the method according to the present invention neither involves the lysis of cells nor the numerical determination of an absorbance value caused by an analyte/biomolecule dissolved in the (liquid) sample. In one embodiment, the method according to the present invention does not involve the numerical determination of a light scattering value caused by an analyte or cell or particle in the (liquid) sample. In embodiments, where the number of cells or particles is determined, such number of cells preferably is an integer value.

In one embodiment, the method of the present invention comprises further analysis of the sample, such as the analysis/evaluation of cell motility;
cell morphology;
cell viability;
further characteristics, such as cell acrosome integrity, cell mitochondrion activity, cell deoxyribonucleic acid integrity. Such characteristics may be used to classify cells and distinguish between cells to be counted and cells not to be counted. These characteristics may be used to determine whether or not a cell is to be counted towards the number of cells to be measured. For example, a cell, e. g. a spermatozoon, which is immobile or not viable may, in one embodiment, not be counted towards the number of cells to be measured. Depending on the chosen characteristics/parameters, different subsets of cells in a sample may be counted.

FURTHER DESCRIPTION OF PREFERRED EMBODIMENTS

The counting compartment of the present invention was developed due to the following critical features of single-use or one-way devices, which are for example:

requirement that the indicated depth is maintained for quantitative evaluation of a sample;
the way of loading the device as well as the quality of the sample can influence the result of such an evaluation;
requirement of evenness or planarity of the plates/glasses;
sample compatibility (such as sperm compatibility) of the materials;
for each sample, a new one-way device needs to be used;
will the cells or particles of the sample be evenly distributed in the counting department?

The present invention provides a counting compartment or chamber and respective counting device which can be permanently used,
reliably measures samples, such as the number of sperm cells in a sperm sample, or the concentration and motility of sperm samples,
can be used in a simple and automated way.

The counting compartment or chamber and respective counting device of the present invention can be used manually and in an automated manner. In the following an automated embodiment is further explained:

Set-Up of the Counting Compartment or Chamber

Figure 2:
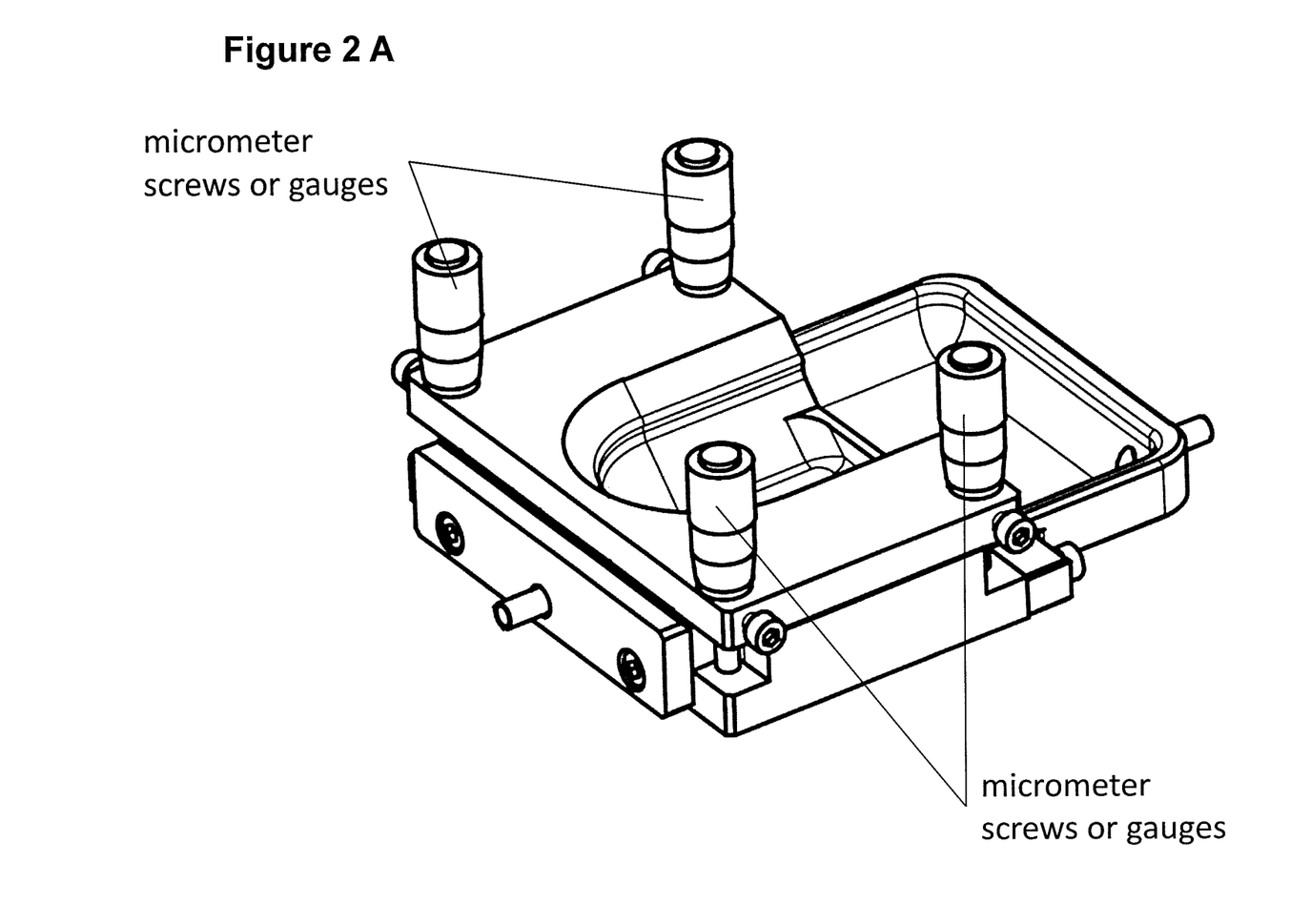
FIG. 2. A preferred embodiment of the counting compartment.

The counting compartment or chamber includes a bottom and lid part. The lid part includes micrometer screws or gauges and a measurement window. The bottom part includes a similar configured measurement window. Furthermore, magnetic means and spacer are integrated in the bottom part. The bottom part furthermore includes an outlet area.

For details, please see FIGS. 2A to 2C.

The Measurement Window

The measurement windows (made of glass or plastic) are configured such that in the middle there is a step (for example, in the range of 5 to 10 µm, such as a 5 µm, 6 µm or 7 µm high step). When the measurement windows are set into the lid and bottom part, the measurement windows are aligned/oriented that both steps are congruent (i.e. superimposed) and in the directed of the sample flow. The steps are super-imposed, thereby forming two different heights/depths of the counting compartment, which differ in height by the sum of the steps in the measurement windows (for example, the sum can be in the range of 10 to 20 µm, such as 10 µm, 12 µm or 14 µm) (see FIG. 1A).

Periphery of the Counting Compartment or Chamber (i.e. the Counting Device)

Figure 3:
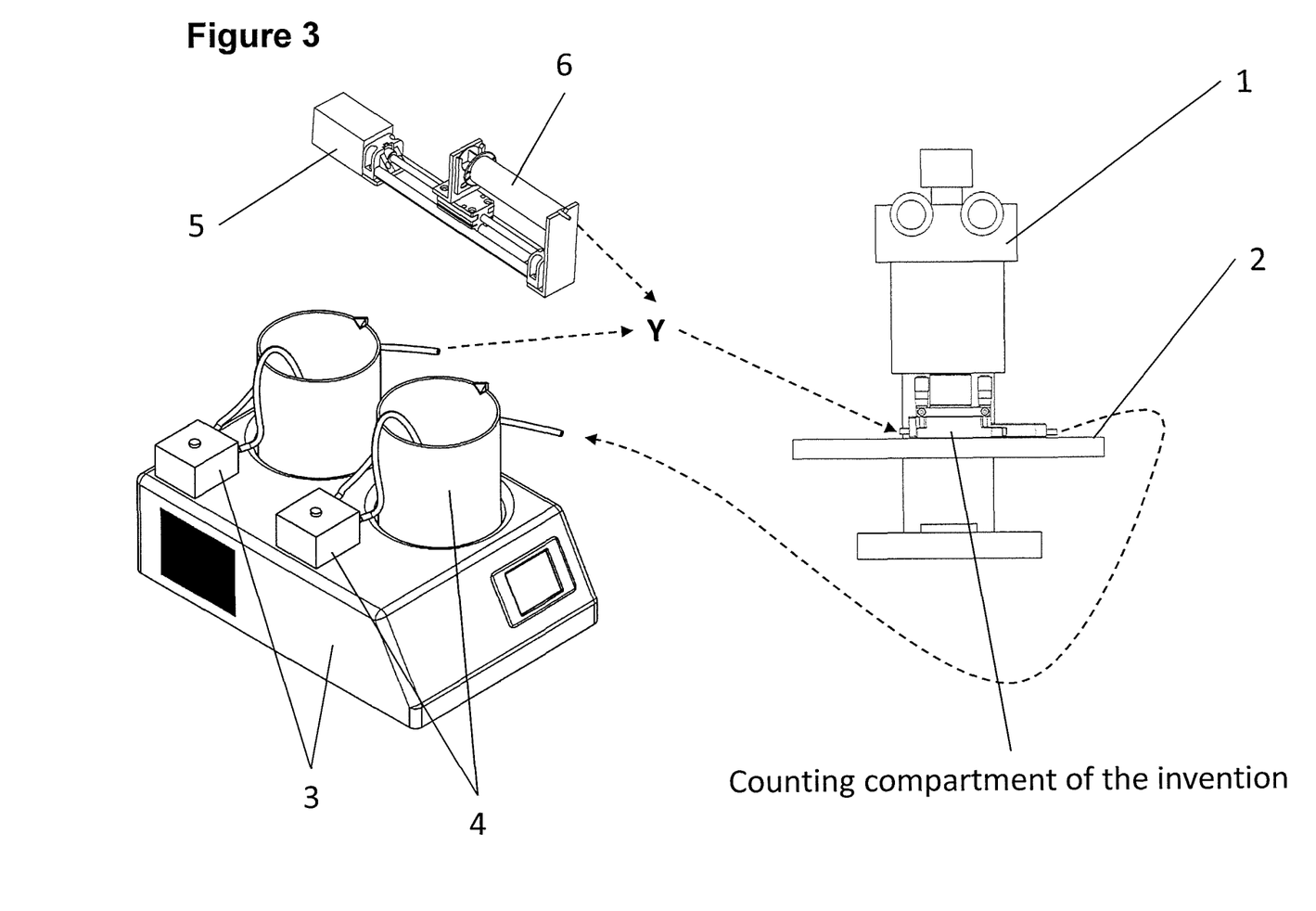
FIG. 3. An exemplary embodiment of the counting device.

For use, the counting compartment is positioned on a heatable motorized positioning unit underneath a light microscope with negative phase contrast (see FIG. 3). Furthermore, the counting compartment is connected to a draw-off pump, a control unit, an injection pump (with e.g. sample syringe connected thereto).

Mode of Operation of the Counting Compartment or Chamber

The functional core of the counting compartment is the volume which is formed by the overlapping measurement windows of lid and bottom part. The distance of both measurement windows to each other is adjusted, namely plan-parallel to each other, by the micrometer screws/gauges integrated in the lid. This is carried out by a continuous white-light interferometry measurement. Generally, depths between about 5 µm to 100 µm, preferably 10 to 40 µm are set (adjusted).

Opening and closing of the counting compartment is carried out by magnetic means, such as permanent electro magnets located in the bottom part.

For example, the magnetic means can function in the following way: If no electric current is applied, the lid is pulled towards the bottom, such that the counting compartment is closed. If electric current is applied, the magnetic means lose their holding force, such that the lid part is lifted, and the counting compartment is open. In case the electric power is turned off, the counting compartment closes.

Liquids are only loaded when the counting compartment is open. The loading usually is carried out via silicone tubing, wherein a y-angle, which is located upstream of the counting compartment, unites/brings together sample liquid and washing liquid (such as diluent in case of semen samples) into the inlet of the counting compartment.

Injection of the sample is carried out using an injection pump, in which a milliliter syringe filled with sample liquid is placed. The washing or rinsing liquid is pumped into the counting compartment when needed via a flexible-tube pump located e.g. in the housing of the control unit. Said pump uses washing liquid (such as diluent in case of semen samples).

Downstream of the counting compartment is a draw-off pump, which is connected to the outlet via silicone tubing and which draws off waste or superfluous liquid from the counting compartment.

The whole process is controlled by a (central) control unit.

Said central control unit can be connected to and communicate with a processing, analyzing and/or evaluating system and software, such as Androvision®, for further automation. Then, only one start signal could be required.

Mode of Operation of the Step-Measurement Windows

When a processing, analyzing and/or evaluating system and software, such as Androvision®, is used, a specific amount of measurement fields with the bigger depth and the same amount of measurement fields with the smaller depth are analyzed, such as with regard to the cell number/count (e.g. sperm number). See e.g. FIG. 4.

Figure 4:
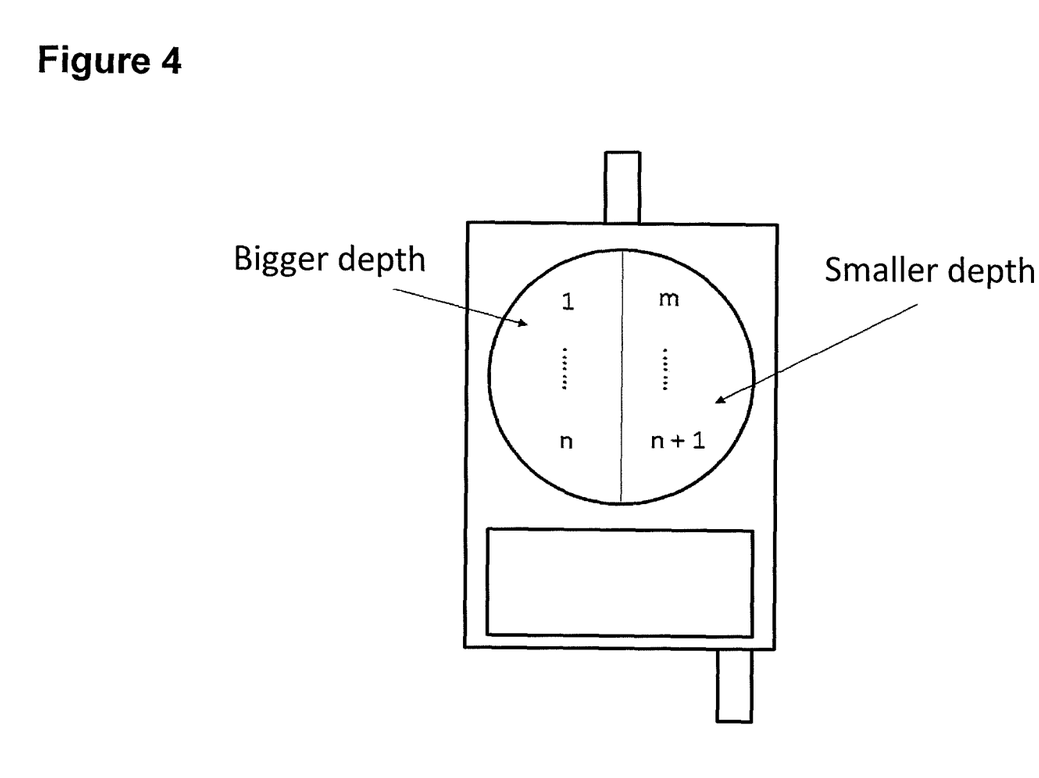
FIG. 4. Schematic view of the arrangement of measurement fields during an analysis with an evaluating system and software.

For the results determined for each measurement field for the bigger and the smaller depth the respective average is determined (one average value for the bigger and one for the smaller height/depth). Thus, two different values are obtained. For example, two different spermatozoa concentrations (since spermatozoa concentration is linearly dependent on the measurement volume). Furthermore, also the total number of cells or particles (such as sperm cells) in each measurement field are averaged. Thus, an average cell/particle count for the bigger depth and an average cell/particle count for the smaller depth are obtained. Then, the difference between these two values is obtained (keeping in mind the difference between the two depths, which is the sum of the steps in the measurement windows) and, thus, a third cell/particle count is obtained, which can be the result of the measurement or it can be used as a control for the other obtained results.

The advantages of such difference measurement are that the measurement depth does not need to be adjusted for each measurement and that possible errors in the measurement depth, which can e.g. be caused by foreign particles/impurities in the sample, are recognized or "masked", since the difference between the smaller and the bigger height/depth is constant.

Figure 5:
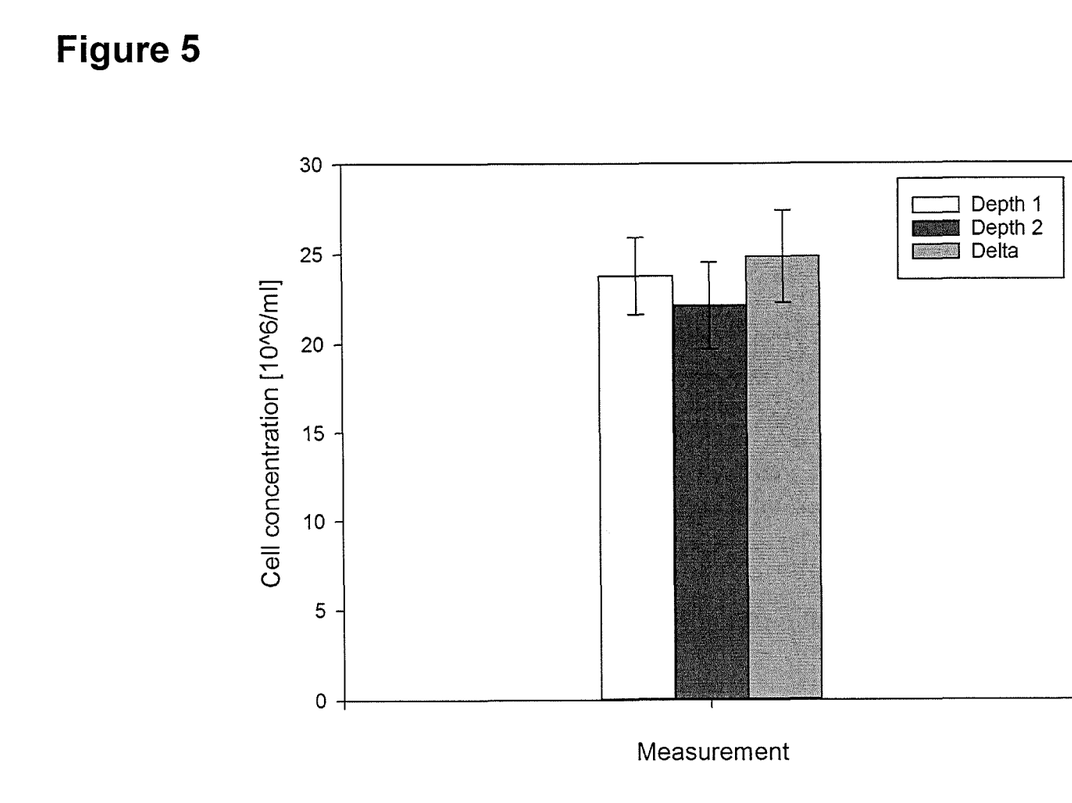
FIG. 5. Example of an analysis.

Thus, the third value (i.e. the difference between the (averaged) value of the smaller and the bigger measurement depth) provides the desired value, such as the sperm concentration, or at the same time can serve as control of the other two values, since all values should provide the same number of sperm per volume unit. See e.g. FIG. 5.

Furthermore, in the smaller measurement depth, a morphological analysis is possible, such as morphological analysis of (sperm) cells.

Advantages of the Counting Compartment or Chamber
  precise measurement of concentration of a sample, such as sperm concentration, and further features of the sample, such as sperm motility;
  can be re-used permanently, thereby reducing costs in a routine laboratory use;
  automatized use, thereby avoiding errors of the user;
  can be connected and integrated with a processing, analyzing and/or evaluating system and software (such as Androvision® CASA system of Minitüb GmbH, Germany).

The following examples and drawings illustrate the present invention without, however, limiting the same thereto.

BRIEF DESCRIPTION OF THE DRAWINGS

(A) In one embodiment, the bottom and top measurement window each comprise a step. The counting compartment is configured such that when the lid/top part closes on the bottom part the step of each of both measurement windows is on top of each other (i.e. super-imposed), thereby forming two different depths.

(B) In one embodiment, one of the bottom or top measurement window is placed with inclination.

(C) In one embodiment, one of the bottom or top measurement window is placed parallel to the other measurement window and is provided with an inclined plane on the side facing the sample liquid.

(D) In one embodiment, the at least two different depths are provided by movement, such as with a spindle with motor.

(A) The top or lid part comprising a top measurement window and micrometer screws or gauges, wherein the top or lid part is situated on the bottom part.

(B) The bottom part comprising a bottom measurement window, permanent electro magnets, spacer and an outlet.

(C) The top or lid part comprising a top measurement window.

The counting device comprising a phase contrast light microscope (1), scan stage unit (2), control unit with pump (3), draw-off pump with container (4), injection pump (5), injection syringe for sample (6). The counting device is connected to a processing, analyzing and/or evaluating system and software, in particular AndroVision® CASA Software (Minitüb GmbH, Germany).

(in particular AndroVision® CASA Software), wherein
m number of measurement fields, and
n=number of measurement fields for each depth.

Shown is the determination of a cell concentration in a sample.

EXAMPLES

Example 1 Measurement Conditions

The counting compartment can be used for sample analyses after cleaning and rinsing.

Furthermore, the compartment has to warm up on a certain temperature which can generally be achieved by using a heating unit integrated into the microscope. For semen samples the temperature should simulate physiological conditions (e.g. between 35° C. and 39° C.).

Cleaning can be conducted by using alcoholic derivatives and rinsing by using a washing liquid such as BTS semen extender in case of semen samples. The amount of washing liquid should be sufficiently chosen in order to remove the amount of sample material in the counting compartment.

The counting compartment has to be opened for rinsing i.e. the lid or top part is in open position.

After homogenizing a sufficient amount of sample can be injected into the counting compartment. The counting compartment has to be open during sample injection. Analyses can follow.

After finishing analyses the compartment is opened again and rinsed for the next sample.

The procedure starts from the beginning but without the cleaning step which is only necessary before using the compartment for the first time.

Example 2 Sample Treatment

In case of semen samples, the raw ejaculate is appropriately diluted with extenders, such as Androhep® Plus (Minitüb GmbH, Germany), Androstar® Plus (Minitüb GmbH, Germany), M III® (Minitüb GmbH, Germany) or BTS (Minitüb GmbH, Germany), shortly after collecting the ejaculate. For example, an appropriate dilution can be one part raw ejaculate and nine parts of extender, depending on the animal species and expected semen concentration of the ejaculate.

Homogenization of such a diluted sample, especially before using the counting compartment, can be conducted manually or mechanically.

Manual homogenization includes shaking the sample and/or turning the sample in a container. Mechanical homogenization includes the usage of a vortex mechanical mixer or a magnetic stirrer.

The features disclosed in the foregoing description, in the claims and/or in the accompanying drawings may, both separately and in any combination thereof, be material for realizing the invention in diverse forms thereof.

The invention claimed is:

1. A flow-through counting compartment for analyzing samples comprising cells or particles,
    said counting compartment comprising:
    (1) a lid or top part comprising a top measurement window;
    (2) a bottom part comprising a bottom measurement window; and
    (3) at least two different depths provided by the bottom and top measurement windows,
    wherein the bottom and/or top measurement window comprises one or more steps.

2. The flow-through counting compartment of claim 1, wherein the at least two different depths provided by the bottom and top measurement window are achieved by
    (i) the bottom and/or top measurement window comprise step(s); or
    (ii) one of the bottom or top measurement window is placed with inclination; or
    (iii) one of the bottom or top measurement window is placed parallel to the other measurement window and is provided with an inclined plane on the side facing the sample liquid; or
    (iv) moving the lid or top part and/or the bottom part of the counting compartment.

3. The flow-through counting compartment of claim 1, further comprising:
    means for moving the lid or top part;
    an inlet and outlet;
    a heating unit for controlling the temperature of the sample to be analyzed, and/or
    a positioning unit for moving the counting compartment.

4. The flow-through counting compartment of claim 3, wherein the means for moving the lid or top part comprise magnetic means that are in the lid or top part and/or the bottom part.

5. The flow-through counting compartment of claim 1, wherein the bottom or top measurement window are made of a transparent material.

6. The flow-through counting compartment of claim 1, wherein the at least two different depths provided by the bottom and top measurement window are in the range of about 5 to about 100 µm,
    and/or wherein the difference between the two different depths provided by the bottom and top measurement window is at least the size or height of a monolayer of the cells or particles of the sample to be analyzed.

7. A method for analyzing a sample comprising cells or particles, using the flow-through counting compartment of claim 1 comprising the step of
    determining the difference between the value measured at the at least two different depths of the counting compartment.

8. The method of claim 7, comprising the steps of
    (1) providing a sample comprising cells and/or particles to be analyzed;
    (2) providing the counting compartment;
    (3) loading the counting compartment with the sample, wherein the lid or top part is in open position;
    (4) closing the counting compartment by closing the lid or top part;
    (5) determining the sample value to be measured at the first depth of the at least two different depths and at the second depth of the at least two different depths;
    (6) determining the difference between the two values measured in step (5) and obtaining the sample value;
    (7) opening the counting compartment by opening or lifting the lid or top part; and
    (8) rinsing the counting compartment and thereby removing the sample.

9. The method of claim 8, wherein the sample is homogenized.

10. A counting device for analyzing samples comprising cells or particles comprising:
    a counting compartment,
    a control unit,
    filling means,
    removing means,
    a light microscope and/or a fluorescence microscope, and,
    one or more sensors,
    wherein said counting compartment comprises:
    (1) a lid or top part comprising a top measurement window;
    (2) a bottom part comprising a bottom measurement window; and
    (3) at least two different depths provided by the bottom and top measurement windows,
    wherein the bottom and/or top measurement window comprises one or more steps.

11. The counting device of claim 10, further comprising processing, analyzing and/or evaluating system and software.

12. The counting device of claim 10, which is automated.

13. The counting device of claim 10, comprising a phase contrast microscope comprising a motorized positioning unit, and/or a heating unit; and a white-light interferometer sensor, current sensor, inductive sensor, capacitive sensor or optical sensor.

14. A method for analyzing samples comprising cells or particles, comprising the step of controlling the depth of a counting compartment or sensor measurement, comprising the steps of:
    (1) providing a sample comprising cells and/or particles to be analyzed;
    (2) providing a counting compartment comprising a marking in the lid and a marking in the bottom or in its measurement windows (which allows z axis-calibration), and/or
    providing a counting compartment or device comprising a sensor (such as a white-light interferometer sensor, current sensor, capacitive sensor or laser sensor),
    (3) loading the counting compartment with the sample,
    (4) measuring the distance between the marking in the lid and the marking in the bottom or in its measurement windows (i.e. z axis-calibration) or by measuring the depth with the sensor;
    and then determining the depth of the loaded counting department;
    optionally comprising the use of a correction value or factor;
    (5) determining the sample value(s) to be measured,
    (6) opening the counting compartment by opening or lifting the lid or top part;
    (7) rinsing the counting compartment and thereby removing the sample.

15. The method of claim 14, wherein the samples comprising cells or particles are
- semen samples
- blood samples,
- samples comprising particles,
- samples of microorganisms, or
- algae samples.

16. The method, according to claim 15, wherein the sample value to be measured is the number of cells or particles in the sample.

17. The method of claim 14, further comprising analysis of
- cell motility;
- cell morphology;
- cell viability;
- cell acrosome integrity; cell mitochondrion activity; and/or cell deoxyribonucleic acid integrity.

18. The method of claim 14, wherein controlling the depth of the counting compartment is done by z-axis calibration.

19. The method of claim 14, wherein the sensor measurement is done by using a white-light interferometer sensor, current sensor, capacitive sensor or laser sensor.

\* \* \* \* \*